US009101964B2

(12) United States Patent
Hunter et al.

(10) Patent No.: US 9,101,964 B2
(45) Date of Patent: Aug. 11, 2015

(54) METHOD FOR SORTING RESISTANT SEED FROM A MIXTURE WITH SUSCEPTIBLE SEED

(71) Applicant: PIONEER HI-BRED INTERNATIONAL, INC., Johnston, IA (US)

(72) Inventors: James L. Hunter, Littleton, CO (US); Gregory K. Mangold, Johnston, IA (US)

(73) Assignee: PIONEER HI BRED INTERNATIONAL INC, Johnston, IA (US)

( * ) Notice: Subject to any disclaimer, the term of this patent is extended or adjusted under 35 U.S.C. 154(b) by 112 days.

(21) Appl. No.: 13/886,827

(22) Filed: May 3, 2013

(65) Prior Publication Data

US 2013/0240414 A1     Sep. 19, 2013

Related U.S. Application Data

(60) Division of application No. 12/974,513, filed on Dec. 21, 2010, now Pat. No. 8,459,463, which is a continuation of application No. 12/571,534, filed on Oct. 1, 2009, now abandoned, which is a continuation-in-part of application No. 12/108,198, filed on Apr. 23, 2008, now Pat. No. 8,626,337.

(60) Provisional application No. 60/913,562, filed on Apr. 24, 2007.

(51) Int. Cl.
  *B07C 5/00*   (2006.01)
  *B07C 5/342*  (2006.01)
  *G01N 21/64*  (2006.01)
  *G01N 21/85*  (2006.01)

(52) U.S. Cl.
  CPC .......... *B07C 5/3427* (2013.01); *G01N 21/6428* (2013.01); *G01N 21/85* (2013.01)

(58) Field of Classification Search
  USPC ........................ 209/47, 49, 51, 552, 936, 938
  See application file for complete search history.

(56) References Cited

U.S. PATENT DOCUMENTS 2,152,758 A    4/1939  Cox
4,368,591 A    1/1983  Barke et al.
(Continued)

FOREIGN PATENT DOCUMENTS

CN    1485803 A      3/2004
EP    0 130 715 A2   1/1985
(Continued)

OTHER PUBLICATIONS

International Preliminary Report and Written Opinion for Application No. PCT/US2011/066084; dated Jun. 25, 2013.
(Continued)

*Primary Examiner* — Terrell Matthews
(74) *Attorney, Agent, or Firm* — Pioneer Hi-Bred Intl, Inc.

(57) ABSTRACT

The invention generally relates to a novel method of sorting seed by providing a first seed population with a fluorescent indicator and a second seed population visually identical to the first seed population under standard operating conditions. The seed populations are combined to provide a combined seed population. A lamp having an output corresponding to the activation wavelength of the fluorescent indicator and a color sorting system are paired to count or separate the seed populations, as desired.

22 Claims, 2 Drawing Sheets

(56) References Cited

U.S. PATENT DOCUMENTS

| | | | |
|---|---|---|---|
| 4,630,736 A | | 12/1986 | Maughan et al. |
| 4,635,215 A | | 1/1987 | Friend |
| 4,723,661 A | | 2/1988 | Hoppmann et al. |
| 4,975,364 A | * | 12/1990 | Taylor et al. ............... 435/4 |
| 5,412,219 A | | 5/1995 | Chappelle et al. |
| 5,441,735 A | | 8/1995 | Takahara et al. |
| 5,550,318 A | * | 8/1996 | Adams et al. ............ 800/300.1 |
| 5,616,082 A | | 4/1997 | Kobetsky |
| 5,703,784 A | * | 12/1997 | Pearson ..................... 700/223 |
| 5,746,022 A | | 5/1998 | Brown et al. |
| 5,750,340 A | | 5/1998 | Kim et al. |
| 5,862,919 A | | 1/1999 | Eason |
| 5,865,990 A | | 2/1999 | Novak et al. |
| 5,916,029 A | | 6/1999 | Smith et al. |
| 5,929,307 A | | 7/1999 | Hodges et al. |
| 5,973,286 A | | 10/1999 | Wan |
| 6,022,689 A | | 2/2000 | Sarto et al. |
| 6,080,950 A | | 6/2000 | Jalink |
| 6,156,699 A | | 12/2000 | Johnson et al. |
| 6,307,123 B1 | | 10/2001 | Kriz et al. |
| 6,433,252 B1 | | 8/2002 | Kriz et al. |
| 6,627,799 B1 | | 9/2003 | Mariani et al. |
| 6,635,840 B1 | | 10/2003 | Mailloux |
| 6,646,264 B1 | | 11/2003 | Modiano et al. |
| 6,706,989 B2 | | 3/2004 | Hunter et al. |
| 6,734,383 B1 | | 5/2004 | Calcoen et al. |
| 6,865,556 B2 | | 3/2005 | Penner et al. |
| 6,936,827 B1 | | 8/2005 | Mohler |
| 6,947,144 B2 | | 9/2005 | Kim et al. |
| 7,073,653 B2 | | 7/2006 | Hibari |
| 7,086,269 B2 | | 8/2006 | Sauder et al. |
| 7,591,374 B2 | * | 9/2009 | Hunter et al. ............ 209/3.3 |
| 7,703,238 B2 | | 4/2010 | Deppermann et al. |
| 2001/0053958 A1 | | 12/2001 | Ried et al. |
| 2002/0144458 A1 | | 10/2002 | Hunter et al. |
| 2003/0005626 A1 | | 1/2003 | Yoneda et al. |
| 2003/0135888 A1 | | 7/2003 | Zhu et al. |
| 2003/0142852 A1 | | 7/2003 | Lu et al. |
| 2003/0148258 A1 | | 8/2003 | Kim et al. |
| 2003/0233670 A1 | | 12/2003 | Edgerton et al. |
| 2004/0034268 A1 | | 2/2004 | Dell et al. |
| 2004/0118754 A1 | | 6/2004 | Hunter et al. |
| 2004/0205839 A1 | | 10/2004 | Doutriaux et al. |
| 2005/0032033 A1 | * | 2/2005 | Winterboer et al. ............ 435/4 |
| 2005/0114923 A1 | * | 5/2005 | Blaylock et al. ............ 800/282 |
| 2005/0224510 A1 | | 10/2005 | Remis et al. |
| 2006/0032421 A1 | | 2/2006 | Sauder et al. |
| 2006/0042528 A1 | | 3/2006 | Deppermann |
| 2006/0046244 A1 | * | 3/2006 | Deppermann .................. 435/4 |
| 2006/0112628 A1 | | 6/2006 | Kotyk et al. |
| 2007/0077572 A1 | * | 4/2007 | Tawfik et al. .................. 435/6 |
| 2007/0261939 A1 | | 11/2007 | Charpentier |
| 2008/0034652 A1 | | 2/2008 | Hunter et al. |
| 2008/0035532 A1 | | 2/2008 | Hunter et al. |
| 2008/0179226 A1 | | 7/2008 | Hunter et al. |
| 2008/0226753 A1 | | 9/2008 | Cosgrove |
| 2008/0244765 A1 | * | 10/2008 | Zhao et al. .................... 800/260 |
| 2008/0289061 A1 | | 11/2008 | Penner et al. |
| 2008/0310674 A1 | * | 12/2008 | Modiano et al. ............ 382/100 |
| 2008/0317279 A1 | | 12/2008 | Deppermann et al. |
| 2009/0032441 A1 | * | 2/2009 | Corak et al. .................... 209/3.3 |
| 2009/0041869 A1 | | 2/2009 | Cosgrove |
| 2009/0119986 A1 | | 5/2009 | Hunter et al. |
| 2009/0260281 A1 | | 10/2009 | Conrad |
| 2010/0143906 A1 | * | 6/2010 | Becker et al. .................... 435/6 |
| 2010/0281771 A1 | | 11/2010 | Kudo et al. |
| 2011/0202169 A1 | * | 8/2011 | Koehler et al. ............... 700/215 |

FOREIGN PATENT DOCUMENTS

| | | |
|---|---|---|
| GB | 954333 | 4/1964 |
| JP | 63143087 | 6/1988 |
| JP | 10-309538 A | 11/1998 |
| WO | WO-85/00122 A1 | 1/1985 |
| WO | WO-2008/080166 A2 | 7/2008 |
| WO | WO-2008/085729 A2 | 7/2008 |
| WO | WO-2008/134347 A2 | 11/2008 |

OTHER PUBLICATIONS

Jach et al., "Use of Red Fluorescent Protein from *Discosoma* sp. (dsRED) as a Reporter for Plant Gene Expression," *The Plant Journal*, vol. 28, No. 4, 2001, pp. 483-491.

Melamed-Bessudo et al., "A New Seed-Based Assay for Meiotic Recombination in *Arabidopsis thaliana*," *The Plant Journal*, vol. 43, No. 3, Aug. 2005, pp. 458-466.

Nishizawa et al., "A Red Fluorescent Protein, DsRed2, as a Visual Reporter for Transient Expression and Stable Transformation in Soybean," *Plant Cell Reports*, vol. 25, No. 12, Jul. 14, 2006, pp. 1355-1361.

Stuitje et al., "Seed-Expressed Fluorescent Proteins as Versatile Tools for Easy (Co)transformation and High-Throughput Functional Genomics in *Arabidopsis*," *Plant Biotechnology Journal*, vol. 1, 2003, pp. 301-309.

Wenck et al., "Reef-Coral Proteins as Visual, Non-Destructive Reporters for Plant Transformation," *Plant Cell Reports*, vol. 22, No. 4, Nov. 1, 2003, pp. 244-251.

Grainger: Laser Glasses, Red, [online] [retrieved Nov. 13, 2008]; Retrieved from internet: <URL: http://www.grainger.com/Grainger/wwg/search.shtml?searchQuery=3xa22&op—search&Ntt=3xa22 &N=0&GlobalSearch=true&sst=subset > pp. 1-2.

International Search Report and Written Opinion for International Appl. No. PCT/US2008/061238, mailed Dec. 12, 2008.

International Search Report and Written Opinion for Application No. PCT/US2010/051078 dated Mar. 24, 2011.

International Search Report and Written Opinion of the International Searching Authority for Application No. PCT/US2011/066084, dated Aug. 24, 2012.

Office Action from related Chinese Patent Application No. 200880021834.3, issued Jan. 20, 2011.

"Optical Sorter," <http://www.midwestseed.com/seervices/optical_sorter.asp>, printed Dec. 28, 2006.

Partial International Search Report for International Appl. No. PCT/US2008/061238, mailed Sep. 25, 2008.

"Satake Vision Systems," <http://www.satake-usa.com/pdf/SMII_scanmaster_sorter%20.pdf>, printed Dec. 27, 2006.

\* cited by examiner

METHOD FOR SORTING RESISTANT SEED FROM A MIXTURE WITH SUSCEPTIBLE SEED

CROSS-REFERENCE TO RELATED APPLICATIONS

This application is a divisional of U.S. patent application Ser. No. 12/974,513, filed Dec. 21, 2010, which is a continuation of U.S. patent application Ser. No. 12/571,534, filed Oct. 1, 2009, and a continuation-in-part of U.S. patent application Ser. No. 12/108,198, filed Apr. 23, 2008, which claims priority to U.S. Provisional Patent Application No. 60/913,562, filed Apr. 24, 2007. Each of these applications is incorporated by reference herein in its entirety.

BACKGROUND OF THE INVENTION

Insects, nematodes, and related arthropods annually destroy an estimated 15% of agricultural crops in the United States and even more than that in developing countries. In addition, competition with weeds and parasitic and saprophytic plants account for even more potential yield losses.

Some of this damage occurs in the soil when plant pathogens, insects and other such soil borne pests attack the seed after planting. In the production of corn, for example, much of the rest of the damage is caused by rootworms—insect pests that feed upon or otherwise damage the plant roots; and by cutworms, European corn borers, and other pests that feed upon or damage the above ground parts of the plant. General descriptions of the type and mechanisms of attack of pests on agricultural crops are provided by, for example, Metcalf (1962) in Destructive and Useful Insects: Their Habits and Control, Fourth Edition. (Earlier editions by C. L. Metcalf and W. P. Flint) McGraw-Hill Book Company; New York, San Francisco, Toronto, London.; and Agrios, (1988) in Plant Pathology, 3.sup.rd Ed., Academic Press.

Lepidopteran insects cause considerable damage to maize crops throughout North America and the world. One of the leading pests is *Ostrinia nubilalis*, commonly called the European Corn Borer (ECB). Genes encoding the crystal proteins Cry1A(b) and Cry1A(c) from Bt have been introduced into maize as a means of ECB control. The Cry1 group includes, but is not limited to, Cry1A(a), Cry1A(b) and Cry1A(c). See Hofte et al (1989) Microbiol Rev 53: 242-255. These transgenic maize hybrids have been effective in control of ECB (U.S. Pat. Nos. 6,180,744, 5,689,052 and U.S. publication 2002/013227). Recently, Cry1F expressing maize hybrids have also been developed for control of ECB (Chambers, et al. (1991). J. Bact. 173:3966-3976 and Herman, et al. (2002). J. Agric. Food Chem. 50:7076-7078, U.S. Pat. Nos. 5,691,308, 5,188,960 and WO 99/24581). However, developed resistance to Bt toxins presents a challenge in pest control. See McGaughey et al. (1998) Nature Biotechnology 16: 144-146; Estruch et al. (1997) Nature Biotechnology 15:137-141; Roush et al. (1997) Nature Biotechnology 15 816-817; and Hofte et al (1989) supra.

The primary site of action of Cry1 toxins is in the brush border membranes of the midgut epithelia of susceptible insect larvae such as Lepidopteran insects. Cry1A toxin binding polypeptides have been characterized from a variety of Lepidopteran species. A Cry1A(c) binding polypeptide with homology to an aminopeptidase N has been reported from *Manduca sexta, Lymantria dispar, Helicoverpa zea* and *Heliothis virescens*. See Knight et al. (1994) Mol Micro 11: 429-436; Lee et al. (1996) Appl Environ Micro 63: 2845-2849; Gill et al. (1995) J Biol. Chem 270: 27277-27282; and Garczynski et al. (1991) Appl Environ Microbiol 10: 2816-2820.

Another Bt toxin binding polypeptide (BTR1) cloned from *M. sexta* has homology to the cadherin polypeptide superfamily and binds Cry1A(a), Cry1A(b) and Cry1A(c). See Vadlamudi et al. (1995) J Biol Chem 270(10):5490-4, Keeton et al. (1998) Appl Environ Microbiol 64(6):2158-2165; Keeton et al. (1997) Appl Environ Microbiol 63(9):3419-3425 and U.S. Pat. No. 5,693,491.

A subsequently cloned homologue to BTR1 demonstrated binding to Cry1A(a) from *Bombyx mori* as described in Thara et al. (1998) Comparative Biochemistry and Physiology, Part B 120:197-204 and Nagamatsu et al. (1998) Biosci. Biotechnol. Biochem. 62(4):727-734.

Other serious insect pests of corn in the Midwestern United States are the larval forms of three species of *Diabrotica* beetles. These include the Western corn rootworm, *Diabrotica virgifera virgifera* LeConte, the Northern corn rootworm, *Diabrotica barberi* Smith and *Diabrotica barberi* Lawrence, and the Southern corn rootworm, *Diabrotica undecimpunctata howardi* Barber.

Corn rootworms (CRW) overwinter in the egg state in fields where corn was grown the previous season. The eggs hatch from late May through June. If a corn crop is not followed by another corn crop in the subsequent year, the larvae will die. Accordingly, the impact of corn rootworm is felt most directly in areas where corn is systematically followed by corn, as is typical in many areas of the Midwestern United States.

There is evidence of the emergence of a new race of corn rootworm which ovipositions its eggs for overwintering onto adjacent soybean plants. The most common practice in the mid-western United States has been for fields to be rotated annually with corn, followed the next year with soybeans, in order to manage the development of an epidemic of corn rootworm pressure on fields of corn. While this strategy overall has been successful in reducing the corn rootworm feeding pressure on corn in many areas, the evolutionary emergence of this new race of corn rootworm creates a problem which was not anticipated and which could not have been easily foreseen. This new race, which preferentially deposits its eggs onto soybean fields, provides an unintended feeding pressure on the next year's intended corn crop in the field in which soybeans were grown the previous year, and the subsequent requirement for insecticidal control measures which adds unintended cost to the farmer in the form of additional labor for spraying and additional costs of goods, further reducing the return to the farmer on his/her investment in the crop and harvest.

The western corn rootworm (WCRW), *D. virgifera virgifera*, is a widely distributed pest of corn in North America, and in many instances, chemical insecticides are indiscriminately used to keep the numbers of rootworms below economically damaging levels. In order to assist in the reduction of chemical insecticides used in treatments to control the rootworm population in crop fields, transgenic lines of corn have been developed which produce one of a number of amino acid sequence variants of an insecticidal protein produced naturally in the bacterium *Bacillus thuringiensis*. One such protein, generally referred to as Cry3Bb, has recently been modified by English et al., in U.S. Pat. No. 6,023,013 and related patents and applications, to contain one or more amino acid sequence variations which, when tested in insect bioassay against the corn rootworm, demonstrates from about seven (7) to about ten (10) fold increase in insecticidal activity when compared to the wild type amino acid sequence.

Another Bt toxin that has been found to be effective in transgenic plants for the control of WCRW is Cry34/35 (U.S. Pat. Nos. 6,548,291, 6,083,499, 6,128,180, 6,624,145 and 6,677,148).

As indicated above, one concern is that resistant ECB and WCRW will emerge. One strategy for combating the development of resistance is to select a recombinant corn event which expresses high levels of the insecticidal protein such that one or a few bites of a transgenic corn plant would cause at least total cessation of feeding and subsequent death of the pest.

Another strategy would be to combine a second ECB or WCRW specific insecticidal protein in the form of a recombinant event in the same plant or in an adjacent plant, for example, another Cry protein or alternatively another insecticidal protein such as a recombinant acyl lipid hydrolase or insecticidal variant thereof (WO 01/49834). Preferably the second toxin or toxin complex would have a different mode of action than the first toxin, and preferably, if receptors were involved in the toxicity of the insect to the recombinant protein, the receptors for each of the two or more insecticidal proteins in the same plant or an adjacent plant would be different so that if a change of function of a receptor or a loss of function of a receptor developed as the cause of resistance to the particular insecticidal protein, then it should not and likely would not affect the insecticidal activity of the remaining toxin which would be shown to bind to a receptor different from the receptor causing the loss of function of one of the two insecticidal proteins cloned into a plant. Accordingly, the first one or more transgenes and the second one or more transgenes are each, respectively insecticidal to the same target insect and bind without competition to different binding sites in the gut membranes of the target insect.

Still another strategy would combine a chemical pesticide with a pesticidal protein expressed in a transgenic plant. This could conceivably take the form of a chemical seed treatment of a recombinant seed which would allow for the dispersal into a zone around the root of a pesticidally controlling amount of a chemical pesticide which would protect root tissues from target pest infestation so long as the chemical persisted or the root tissue remained within the zone of pesticide dispersed into the soil.

Because of concern about the impact of chemical pesticides on public health and the health of the environment, significant efforts have been made to find ways to reduce the amount of chemical pesticides that are used. Recently, much of this effort has focused on the development of transgenic crops that are engineered to express insect toxicants derived from microorganisms. For example, U.S. Pat. No. 5,877,012 to Estruch et al, discloses the cloning and expression of proteins from such organisms as *Bacillus, Pseudomonas, Clavibacter* and *Rhizobium* into plants to obtain transgenic plants with resistance to such pests as black cutworms, armyworms, several borers and other insect pests. Publication WO/EP97/07089 by Privalle et al. teaches the transformation of monocotyledons, such as corn, with a recombinant DNA sequence encoding peroxidase for the protection of the uplant from feeding by corn borers, earworms and cutworms, Jansens et al. (1997) Crop Sci., 37(5): 1616-1624, reported the production of transgenic corn containing a gene encoding a crystalline protein from *Bacillus thuringiensis* (Bt) that controlled both generations of ECB. U.S. Pat. Nos. 5,625,136 and 5,859,336 to Koziel et al. reported that the transformation of corn with a gene from *B. thuringiensis* that encoded for delta-endotoxins provided the transgenic corn with improved resistance to ECB. A comprehensive report of field trials of transgenic corn that expresses an insecticidal protein from *B. thuringiensis* has been provided by Armstrong et al., in Crop Science, 35(2):550-557 (1995).

Another alternative to the conventional forms of pesticide application is the treatment of plant seeds with pesticides. The use of fungicides or nematicides to protect seeds, and young roots and shoots from attack after planting and sprouting, and the use of low levels of insecticides for the protection of, for example, corn seed from wireworm, has been used for some time. Seed treatment with pesticides has the advantage of providing for the protection of the seeds, while minimizing the amount of pesticide required and limiting the amount of contact with the pesticide and the number of different field applications necessary to attain control of the pests in the field.

Other examples of the control of pests by applying insecticides directly to plant seed are provided in, for example, U.S. Pat. No. 5,696,144, which discloses that ECB caused less feeding damage to corn plants grown from seed treated with a 1-arylpyrazole compound at a rate of 500 g per quintal of seed than control plants grown from untreated seed. In addition, U.S. Pat. No. 5,876,739 to Turnblad et al. (and its parent, U.S. Pat. No. 5,849,320) disclose a method for controlling soil-borne insects which involves treating seeds with a coating containing one or more polymeric binders and an insecticide. This reference provides a list of insecticides that it identifies as candidates for use in this coating and also names a number of potential target insects.

Although recent developments in genetic engineering of plants have improved the ability to protect plants from pests without using chemical pesticides, and while such techniques such as the treatment of seeds with pesticides have reduced the harmful effects of pesticides on the environment, numerous problems remain that limit the successful application of these methods under actual field conditions.

Application Ser. No. 10/599,307, filed Sep. 26, 2006, describes an improved method for the protection of plants, especially corn plants, from feeding damage by pests. This method reduces the required application rate of conventional chemical pesticides, and also limits the number of separate field operations that are required for crop planting and cultivation.

Mixing of seed samples, as described in application Ser. No. 10/599,307 presents new problems which are sought to be solved by the present application.

In order to ensure adequate application of the mixed seed, individual seeds are to be visually indistinct to a farmer. However, in order to maintain quality control, it is necessary for the seed producer to be able to adequately sample the mixed seed to determine whether the proper ratio is being maintained. Additionally, if seed is returned to the producer without being sold or grown, it is necessary for the seed producer to separate the differing seed types.

This situation is further complicated by regulations, such as the Federal Seed Act as enforced by the Seed Branch of the USDA, which require seed bags to individually identify each seed type present in a bag, as a percentage of the whole, and its germination rate. Unless seeds are in some manner distinguishable from one another, it is impossible to accurately report germination rates and reuse seed. Further, if one seed type has a shorter shelf-life than another, it may be preferable to replace the shorter lived seed while recycling the longer-lived seed. In order to accomplish this, the mixed seed must be easily separable.

Therefore, it is a principle objective of this invention is to provide a method for sorting seeds from one another while maintaining visual indistinctiveness between any two seed types.

It is a further objective of this invention to provide a method of treating one or more fractions of a seed population with an additive to render visually indistinct seed fractions distinctive under specific conditions.

It is a further objective of this invention to provide a method for identifying and quantifying the percentage of differing seed types in a seed sample.

BRIEF SUMMARY OF THE INVENTION

Figure 1:
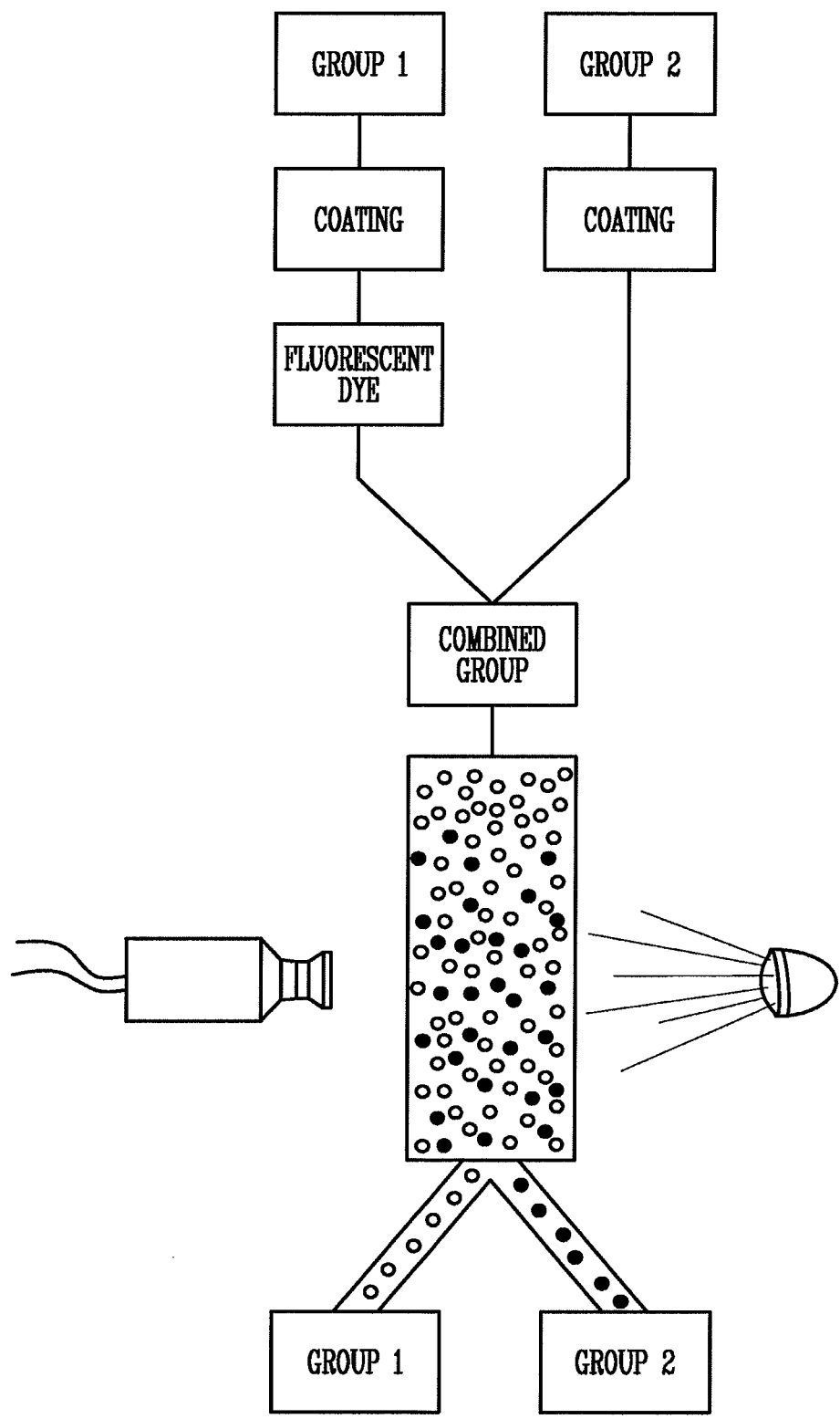
FIG. 1 is a flow chart showing one embodiment of the present invention.

The invention generally relates to a method of sorting seed by providing a first and a second group of seeds, applying an additive, such as a fluorescent dye to one of the groups so as to maintain the two groups as visually indistinct under ambient light conditions. The group is then sampled and passed under a lamp emitting light with wavelengths corresponding to the activation wavelength of the fluorescent dye. While the fluorescent dye is active, the seeds are sorted by a color sorting system.

According to an alternative embodiment, several seed populations are provided, each population having a unique characteristic. All but one of the seed populations are dyed utilizing fluorescent dyes having various activation and/or emission wavelengths. The seed populations are then combined. Sorting of the various seed populations from the combined population is accomplished by providing one or more color sorting devices paired with a lamp having a wavelength corresponding to one or more of the activation wavelengths of the fluorescent dye.

According to an alternative embodiment, a population of genetically modified seeds is provided with a fluorescent genetic marker which has a specific activation and emission wavelength. Non-genetically modified seeds in a second population are colored to visually correspond with the first population. The two populations are combined to produce a combined seed population. Seeds from either of the two populations are separated by a color sorting system with a lamp corresponding to the activation wavelength of the fluorescent marker.

According to an alternative embodiment, instead of sorting the seed a sample of the combined seed population is provided. The sample is counted to determine the number of seeds. A color sorting system and lamp corresponding to a fluorescent dye or marker is utilized to identify the number of seeds having or lacking the fluorescent dye or marker. The system is coupled to an analyzer to determine the relative percentage of each seed type in the combined population. Alternatively, the computer relates this information to a feedback system which is mixing the seed populations.

DETAILED DESCRIPTION

In order to prevent the development of insect resistance to either genetically modified seeds or specific pesticides, it has been proposed to provide a seed bag containing seed containing both resistant and non-resistant seed, see application No. 61/153,689 filed Feb. 19, 2009.

As used in this application, the terms "resistant seed" and "non-susceptible seed," mean seed which is either genetically modified or treated with a specific pesticide to kill or prevent insect or other pest infiltration into the seed or germinating plant.

As used in this application, the terms "non-resistant seed," "susceptible seed," and "refuge" mean seed which is not genetically modified or treated with a specific pesticide to kill or prevent insect or other pest infiltration into the seed or germinating plant.

As used in this application, the term "visually indistinct" is used in conjunction with two or more seed groups, each having a range of colors, where the term "color" is defined by lightness (light versus dark), saturation (intense versus dull), and hue (e.g. red, green, or blue). The term "visually indistinct" means that the two groups, under ambient lighting conditions such as sunlight or indoor lighting, are positively indistinguishable from one another. The range of colors of each group overlap to a significant degree under these conditions, creating the appearance to the human eye of indistinctiveness.

The system is defined so that under specific conditions, such as under a certain wavelength in the visible light spectrum (VLS) or light outside of the VLS, the seed groups exhibit different color characteristics, although hue is the preferred indicator. Two seed groups which are exhibiting these different characteristics are referred to as "optically distinct." This distinctiveness between two seed groups does not have to be in the VLS, and therefore two groups may be simultaneously "visually indistinct" and "optically distinct." One such example is a seed application on one group of seeds which increases the infrared reflectivity of the seed. Within the VLS, the two groups would be visually indistinct, but to a machine reader sensitive to infrared light, the groups would be "optically distinct."

As used in this application, the term "seed application" also has a specific meaning. A seed application defines any external substance applied to a seed. The term includes, without limitation pesticides, biological markers, dyes, fungicides, chemical growth agents, or any other substance helpful to the development of the seed or a detectable substance to create a difference between two seed groups. Additionally, a seed application does not have to completely cover the seed, and is therefore distinct from a seed coating. While some applications may be best applied to the seed by coating the seed completely, it is appreciated that some materials may be selectively applied to less than the entire seed, such as to the crown of the seed. The seed application also does not need to be in direct contact with the seed. It is well known that a first seed application may be applied to a seed and later a second seed application is applied over the first. Therefore, the term seed application is intended to mean any substance applied to the seed, but does not include proteins manufactured by the seed, either naturally or due to genetic engineering. The term also does not apply to genetic modification of the seed prior to its production from a parent plant.

The invention will generally be described as relating to seed mixtures having two types of seeds, one being resistant and the other being non-resistant. However, it can be appreciated that multiple combinations, such as two seeds each having a different resistance characteristic, possibly combined with a third non-resistant seed type, may be used.

According to the first step of the novel method of sorting, at least two seed populations are chosen. The first population is of resistant seed and the second is of susceptible seed. More than two seed groups may also be chosen, each having different desired characteristics, according to the application needs.

Once the seed populations are chosen, both populations are given a seed application. Usually this coats the seed and consists of a pesticidal treatment. This seed application usually is evenly applied to the seeds to create a uniform color among all of the seeds. One of the populations, either susceptible or resistant, is treated with a seed additive such as a fluorescent dye. The Federal Seed Act requires any seed treated with a pesticide to be colored indicating treatment. Therefore, the fluorescent dye should be selected so that when exposed to ambient light it appears the same color as the dyed resistant seed. The two seed populations are visually indistinct, but when exposed to a specific wavelength of light (the activation wavelength) the fluorescent dye emits a different wavelength of light (the emission wavelength) causing the two populations to become optically distinct. This optical distinctiveness is not apparent under ambient conditions even though ambient light may contain light of the activation wavelength. This is due to the low intensity of the light emitted by the activated fluorescent dye relative to the intensity of reflected light. Only when the dye is exposed solely to the activation wavelength is the color difference perceptible. Even then, it may be necessary to include a bandpass filter to block out reflected light of the activation wavelength and allow light of the emission wavelength to pass, based on the requirements of the color sorting system. While it is preferred that the activation wavelength is in the ultraviolet spectrum and the emission wavelength is in the visible spectrum, this is not required.

Fluorescent dyes, in addition to producing a different color under an activation wavelength of light, may also change the color of the dyed seed under normal conditions. Therefore, the seed which is not treated with a fluorescent dye may need to have an additional dye, without fluorescent properties, added to ensure visual indistinctiveness between the two seed populations. Alternatively, the fluorescent dye additive may be selected to be low so that the color difference is virtually undetectable.

If more than two seed populations are chosen, then each seed population has an application and more than one fluorescent dye is used. For example, a first seed population targeting European Corn Borers (ECB), a second seed population targeting western corn rootworm (WCRW), and a third population consisting of refuge might be combined. Two different fluorescent dyes, each having a separate activation and/or emission wavelength, would then be selected. For example, a blue dye having an activation wavelength of 420-450 nm and an emission wavelength of 470-500 nm and a red dye having an activation wavelength of 560-590 nm and an emission wavelength of 590-620 nm might be selected. The first seed population would then be treated with the blue dye, the second seed population with the red dye, and the third population treated without a fluorescent dye, or any alternative combination. The selection of dyes is preferably chosen so that either the activation or emission wavelengths have a difference which allows for sorting, therefore a fluorescent dye should be selected so that the emission wavelength is not significantly absorbed by the components of the additive.

After coating, the seed populations are combined to create a combined seed population. According to one embodiment, the combined seed sample includes 5% susceptible seed and 95% resistant seed, although other combinations are anticipated.

In order to separate the combined seed population into its component parts after combination, color sorting is preferred. Two options are contemplated. First, the seed is sampled and counted to ensure proper combination; and second, the seed is separated, this separation may be done in order to perform testing on each component in a separate step. These separate processes are referred to as counting (FIG. 2) and separating (FIG. 1).

Figure 2:
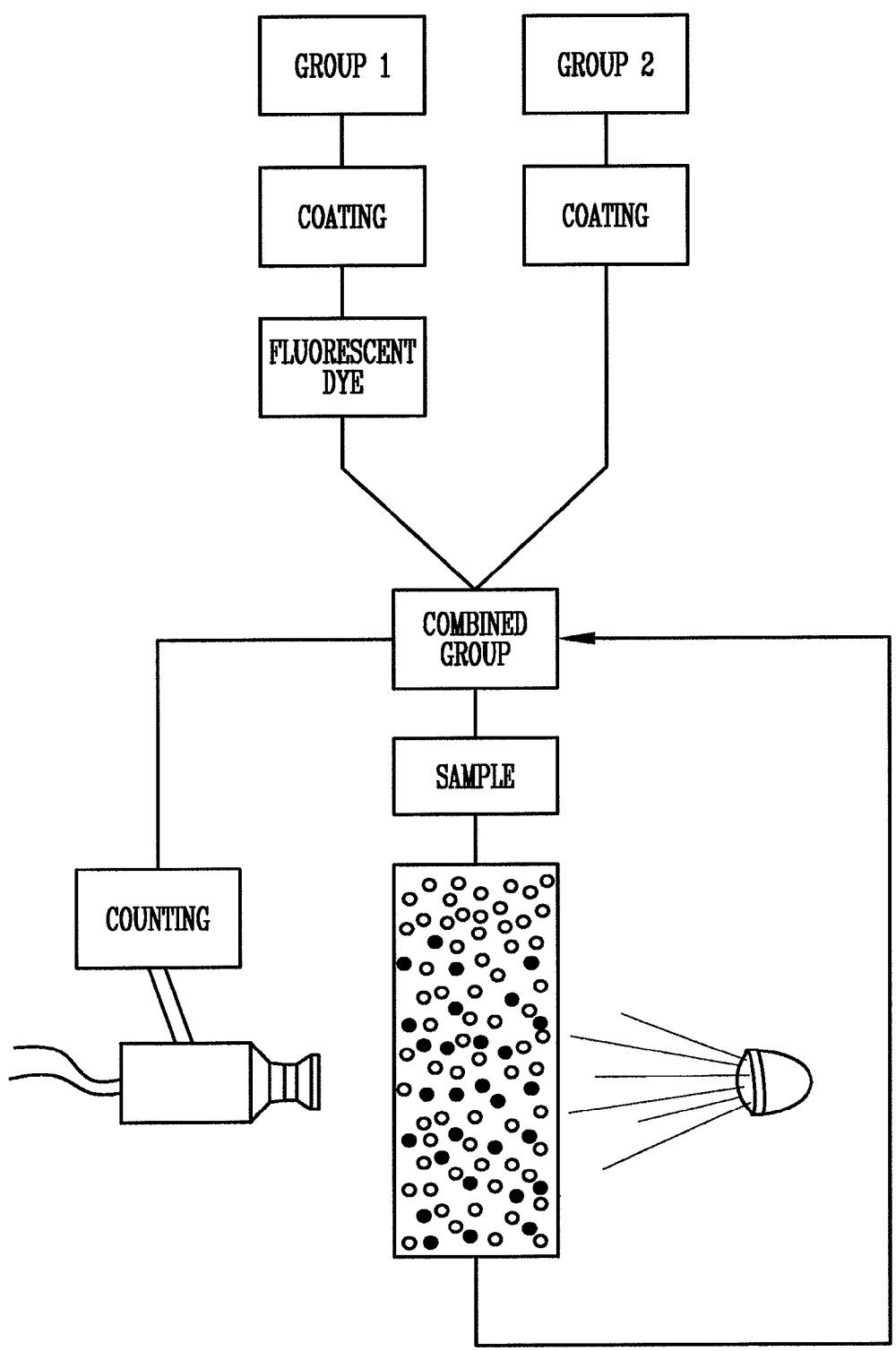
FIG. 2 is a flow chart showing an alternative embodiment of the present invention.

In the counting process, as shown in FIG. 2, a sample (for example 100 seeds) of the combined seed population is removed from the population. The seed is placed on a conveyor belt having a background color closely corresponding to either the neutral color of the seed (or application) or the emission color of the fluorescent dye. The sample is then exposed to a lamp emitting a wavelength corresponding to the activation wavelength of the fluorescent dye. Other wavelengths not corresponding to the activation wavelength are filtered out. This causes the fluorescent dye in one of the seed populations to stand out as they emit light corresponding to the emission wavelength. Seeds not having the fluorescent dye either reflect or absorb the projected activation wavelength, according to their physical properties.

While continuing to be exposed to the light, the sample is passed in front of a camera. The camera transfers the image to color sorting system which recognizes those seeds which are of a different color and provides a count. Since the number of seeds in the sample has been pre-selected—or, alternatively counted in a separate earlier step—the percentage of seeds having the fluorescent dye can be determined.

This counting process is useful in maintaining quality control over a mixing process. The color sorting system could be utilized in a feedback system to constantly monitor the percentage of resistant or susceptible seeds in a sample to ensure that the mixture conforms to a predetermined tolerance, e.g. 95% resistant seed and 5% susceptible seed.

The sorting process, shown in FIG. 1, is substantially identical to the counting process except for the results from the color sorting system. In this process, instead of only providing a count of the marked (or unmarked) seeds, the color sorting system communicates to a sorting machine which separates one seed from another. For one example of a sorting process contemplated by this invention, see application Ser. No. 12/108,198, filed Apr. 23, 2008, herein incorporated by reference in its entirety. One example of software utilized is the Satake Scanmaster system which allows a user to select an intensity value and the required number of adjacent pixels for an object to be sorted. The system fires solenoids which control air jets to separate seeds based upon the occurrence of pixels meeting or exceeding these threshold criteria. Seeds are sorted either light from dark or dark from light, according to preferences and efficiency.

According to the preferred embodiment, a grayscale camera is utilized. Instead of recognizing the color of seeds, the grayscale camera recognizes the lightness or shade of the light reflected from the seed. The background on which the seeds rest is selected to closely match the shade of the seed (or application) not containing a fluorescent dye. Under a lamp projecting the activation wavelength of the fluorescent dye, the non-dyed seed either reflects (showing up as the projected wavelength) or absorbs (appearing black) the light. The conveyor belt is therefore selected according to this shade. The fluorescent dyed seeds fluoresce under this lamp, showing a lighter shade than the surroundings or lighten in order to match the surroundings. The grayscale camera recognizes this lighter or darker shade of the seeds relative to the background, allowing for either counting or sorting. Generally it is preferable to separate the lesser from the greater; if the preferred combination is 5% refuge and 95% resistant seed, the refuge seed should be treated with the fluorescent dye and counted or sorted from the combined population.

The sorting method has been generally described with respect to seed having genetic modification to inhibit certain pests. It is also anticipated that this process may be used with non-genetically modified seed, where all of the seed is genetically identical. According to this embodiment, a single seed population is subdivided into a first and second seed population. One seed population receives a seed application having pesticides, fungicides, or other products beneficial to the growth of the plant. The other seed population receives a seed coating having a neutral, inert, or other reactive substance having a different characteristic than the first. One of the seed populations also receives a fluorescent dye application, while the other is left without a dye, or alternatively, receives an application with a different dye. The seed populations are combined to form a combined seed population. Separation of the seed populations proceeds as indicated above.

The sorting method has also been generally described as applying a separate dye to one of the seed populations. It is also possible to perform the method by utilizing a fluorescent biological marker in one of the seed populations.

The sorting method has also been described as useful with corn seed. While this is the preferred embodiment, the present invention may be applied to other seeds which need to be presented as substantially visually identical while being separable after some time. This method is useful in a variety of applications where seed coating is a preferred method of transferring products to a growing plant. In other seed industries it is common practice to mix varieties of the same or different species into one bag. The seeds may have minute differences which are detectible by a skilled analyst, but such differentiation is intensive and time consuming. Therefore, the process may be used to distinguish between seeds which are not visually identical, but where separation is difficult due to similarities in seed structure. For example, grass seed may consist of several different grass species. Each species of grass may have unique characteristics, but the seeds are close enough to prevent easy distinction. The above-described method may be used to provide a more obvious differentiating characteristics to one or more of the seed types.

A further alternative to the method is utilizing bandpass filters which restrict certain wavelengths of light from passing through. A bandpass filter, corresponding to either the light projected onto the seeds or the emission wavelength, is placed over the camera. Light reflecting off of seeds either having or lacking the dye passes through the bandpass filter to impact the camera. In this manner, the camera only "sees" those seeds which are reflecting light which passes through the bandpass filter. In some cases, a bandpass filter may allow more than one wavelength of light to pass through. This type of filter is particularly useful for sorting of three or more seeds when it is desired to pass or reject seeds having more than one coating. The bandpass filter is preferably configured to pass either light absorbed by the additive or light corresponding to the emission wavelength of a fluorescent dye. If light absorbed by the additive is allowed, then treated seeds show up dark to the camera, while un-treated seeds appear light. If light emitted from the fluorescent dye is allowed to pass, then treated seeds show up light to the camera, while untreated seeds appear dark.

A more sophisticated option for seed sorting, in either binary or multiple cases, the use of a RGB (Red, Green, Blue) camera which is capable of detecting the particular wavelength of light emitted from a seed. Wavelength subsets corresponding to the emission wavelength of various fluorescent dyes or fluorophores are recognized by the RGB camera and associated software. Seeds corresponding to these subsets are sorted into their various groups, providing the desired sort. This approach has been used in the past, but requires greater computational overhead (expense) and is slower than grey scale based sorting techniques.

Other seed applications may be used in lieu of fluorescent dye or biological markers. These include, without limitation, products which: increase ultraviolet or infrared reflectivity or absorption (where the optical distinctiveness occurs outside the VLS); cause phosphorescence (optical distinctiveness is present when a light source is removed); cause chemiluminescence (optical distinctiveness occurs because of light emitted during or following a chemical reaction); change color after exposure to a pretreatment process; exhibit inducible or permanent magnetic properties (where the sorting process would not be based on visual characteristics); or modify the weight of one group relative another group.

The invention has been shown and described above with the preferred embodiments, and it is understood that many modifications, substitutions, and additions may be made which are within the intended spirit and scope of the invention. From the foregoing, it can be seen that the present invention accomplishes at least all of its stated objectives.

What is claimed is:

1. A method of sorting seed comprising the steps of:
providing a first group of seeds having a first seed application comprising an additive;
providing a second group of seeds having a second seed application;
providing a combination seed group consisting of the first and second groups of seeds;
passing part of the combination seed group through a process to create or recognize distinctiveness between the first and second groups based on the additive; and
sorting one of the first or second groups from the combination seed group based on acquired distinctiveness based on the additive.

2. The method of claim 1 wherein the acquired distinctiveness is selected from the group consisting of:
A. fluorescence
B. phosphorescence
C. chemiluminescence
D. U.V. absorption
E. U.V. reflectance
F. infrared reflection
G. infrared absorption
H. inducible or permanent magnetic properties; and
I. color following pretreatment.

3. The method of claim 2 wherein the first and second seed groups are visually indistinct.

4. The method of claim 1 wherein the additive comprises a fluorescent dye having an activation wavelength and an emission wavelength.

5. The method of claim 4 wherein the process to create distinctiveness is exposing the part of the combination seed group to a light corresponding to the activation wavelength.

6. The method of claim 5 wherein the first and second seed groups are visually indistinct before passing the seed group through the process to create distinctiveness.

7. The method of claim 6 wherein the first and second seed groups are sorted based on optical distinctiveness.

8. The method of claim 7 wherein the first and second seed applications comprise a fungicide.

9. The method of claim 7 wherein the first and second seed treatments comprise a pesticide.

10. The method of claim 1 further comprising the steps of:
providing a third seed group having a second additive in the combination seed group;

passing the part of the combined seed group through a second process to create or recognize distinctiveness between the third group and the first and second groups; and sorting the third group from the combination seed group.

11. A method of sorting seed comprising the steps of:
providing a first group of seeds having a first seed treatment comprising an additive;
providing a second group of seeds having a second seed treatment, the second group being visually indistinct from the first group;
combining the first and second groups of seeds to create a combination seed group; and
sorting the first group from the combination seed group based on an optical characteristic created by the additive.

12. The method of claim 11 wherein the additive comprises a fluorescent dye having an activation wavelength and an emission wavelength.

13. The method of claim 12 wherein the optical characteristic is detected for the sorting step by passing the part of the combination seed group past a light corresponding to the activation wavelength of the fluorescent dye.

14. A seed population comprising:
a first seed group having an additive having an activatable color; and
a second seed group,
wherein the first and second groups are visually indistinct.

15. The seed population of claim 14 wherein the first and second seed groups are optically distinct when exposed to a process activating the activatable color of the additive.

16. The seed population of claim 15 wherein the first and second seed groups are combined in a known ratio.

17. The seed population of claim 16 wherein the additive comprises a fluorescent additive having an activation wavelength and an emission wavelength.

18. The seed population of claim 17 wherein the process activating the activatable color comprises exposing the seed group to a light source corresponding to the activation wavelength of the fluorescent additive.

19. The seed population of claim 18 wherein the fluorescent additive is a protein created by a genetic marker in the first group.

20. The seed population of claim 18 wherein the fluorescent additive is a fluorescent dye.

21. The seed population of claim 18 wherein the first and second seed groups are genetically identical and the first seed group comprises a first pesticidal seed treatment and the second seed group comprises a second pesticidal seed treatment.

22. The seed group of claim 18 wherein one of the first and second seed groups comprises a genetically engineered trait.

* * * * *